United States Patent [19]

Cao et al.

[11] Patent Number: 4,507,277

[45] Date of Patent: Mar. 26, 1985

[54] COMPOSITION AND METHOD FOR STIMULATING THE SYNTHESIS OF THE MELANOTIC PIGMENT OF THE SKIN

[75] Inventors: Carlos M. M. Cao; Manuel T. Gonzalez, both of Miramar, Cuba

[73] Assignee: Empresa Cubana Importadora Y Exportadora de Productos Medicos, Havana, Cuba

[21] Appl. No.: 483,283

[22] Filed: Apr. 8, 1983

[51] Int. Cl.³ .................. A61K 7/42; A61K 35/12; A61K 35/48; A61K 37/00
[52] U.S. Cl. .................................. 424/59; 424/95; 424/105; 514/21
[58] Field of Search ............... 424/59, 60, 105, 95, 424/177; 260/112 R, 112.5 R

[56] References Cited

U.S. PATENT DOCUMENTS

| | | | |
|---|---|---|---|
| 4,108,849 | 8/1978 | Thomas | 260/122 |
| 4,219,467 | 8/1980 | Pende et al. | 260/112 R |
| 4,423,036 | 8/1981 | Schneider | 424/105 |

FOREIGN PATENT DOCUMENTS

| | | | |
|---|---|---|---|
| 1492023 | 12/1973 | Fed. Rep. of Germany | 424/59 |
| 2540971 | 3/1977 | Fed. Rep. of Germany | 424/105 |
| 2498451 | 7/1982 | France | 424/59 |
| 142515 | 12/1978 | Japan | 424/105 |

*Primary Examiner*—Esther M. Kepplinger
*Assistant Examiner*—Shawn P. Foley
*Attorney, Agent, or Firm*—Lackenbach, Siegel, Marzullo, Presta & Aronson

[57] ABSTRACT

A composition useful in the treatment of vitiligo, a method for preparing said composition and a method of treating vitiligo with said composition wherein said composition comprises a placental alpha lipoprotein component extracted from placental cotyledons.

6 Claims, No Drawings

COMPOSITION AND METHOD FOR STIMULATING THE SYNTHESIS OF THE MELANOTIC PIGMENT OF THE SKIN

FIELD OF THE INVENTION

This invention relates to the treatment of vitiligo. More particularly, it relates to a composition useful in the treatment of vitiligo, a method for preparing said composition and a method of treating vitiligo with said composition wherein said composition comprises a placental alpha lipoprotein component extracted from placental cotyledons using a solution of benzoic acid in ethanol.

BACKGROUND OF THE INVENTION

Vitiligo is a dermatological illness, due to the absence of melanotic pigments, wherein portions of the body are devoid of color while the surrounding areas are excessively colored. This disease, whose etiology is unknown, afflicts about 1% of the world's population (i.e., about $40 \times 10^6$ persons), with concomitant effects to the afflicted person's psyche and social behavior. Consequently, it has long been desirable to obtain treatments whereby the skin is enabled to regain its normal coloration.

It has long been known to treat vitiligo with psoralens which are either ingested by the patients, or applied to the melanophores wherein the pigment is produced, followed by exposure to ultraviolet (UV) radiation, whereby the melanotic pgiment is produced and the normal coloration of the patient restored.

However, the above methods suffer in that the psoralens are toxic—i.e., they cause dermatitis and necrosis when applied to the skin and hepatitic insufficiency and nervous and digestive disorders when ingested. Furthermore, they require gradually increasing exposures to the ultraviolet radiation, with its concommittant deleterious effects, and their effects are reversible.

It has now been found, in accordance with the present invention, that an irreversible recovery of the patient's normal coloration may be obtained without any of the above adverse reactions.

SUMMARY OF THE INVENTION

It is an object of the instant invention to provide a composition useful in the treatment of vitiligo comprising placental alpha lipoproteins.

It is yet another object of the invention to provide a method for preparing a composition, comprising placental alpha-lipo proteins, useful in the treatment of vitiligo.

According to another object of the invention, there is provided a method for the treatment of vitiligo by use of a composition comprising placental alpha lipoproteins.

Other objects of the invention will be apparent or obvious in accordance with the detailed description of the invention and the claims.

A DETAILED DESCRIPTION OF THE INVENTION

In accordance with the invention, there is provided a composition useful in the treatment of vitiligo, a method for the preparation of said composition, and a method of treating vitiligo with said composition wherein the composition comprises an alpha lipoprotein containing extract from placental cotyledons. Thus, in accordance with the invention, there is provided a composition useful in the treatment of vitiligo comprising at least one placental alpha lipo protein prepared by the steps of (a) congealing placental cotyledons;
(b) triturating and macerating the congealed cotyledons with an ethanol until presence of the lipoprotein in the supernatant liquid is observed;
(c) treating the supernatant liquid with a saturated ethanolic solution of benzoic acid;
(d) washing the precipitate formed in (c) with a saturated aqueous solution of benzoic acid followed by acetone;
(e) redissolving the washed residue in alcohol and filtering on a sodium phosphate buffered Sephadex column;
(f) drying the fraction containing the lipoportein.

The cotyledons useful in connection with the invention may be obtained from the placenta of humans, monkeys, cows, sheep and goats. The placentae used in the practice of the invention are preferably those of human beings.

The cotyledons may be congealed by any methods known in the art including freezing in a refrigerator, by carbon dioxide spray or liquid nitrogen. The preferred method of congealing is to freeze the cotyledons in a refrigerator at about 2° to about 8° C.

The congealing of the cotyledons is effected for about 7 to about 10 days, preferably 7 days.

The maceration and trituration are effected by any means known in the art, until the supernatant liquid is shown to contain the active composition as evidenced by the return of color to a guinea pig's nipple for 20 to 50 days after application of the liquid thereto.

The ethanol used in accordance with any of the processes of this invention may be absolute or an aqueous solution comprising about 70 to about 100% wt 95% wt aqueous ethanol is preferred in accordance with the preferred embodiment of the invention.

The active component is precipitated from the above supernatant liquid by addition of about 5 to about 20 volumes of a saturated ethanolic solution of benzoic acid to about 100 to about 400 volumes of the supernatant liquid.

After filtration, the precipitate is washed with about 200 to about 400 volumes of saturated aqueous benzoic acid per original volume of supernatant liquid of step (b).

The precipitate is then washed, in a centrifuge bottle, with absolute or aqueous acetone. The aqueous acetone may have a concentration in the range of about 70 to about 100% wt and is used in a ratio of about 1 to about 2 volumes per original volume of the supernatant liquid of step (b). The centrifugation is effected at about 1000 to about 3000 RPM for about 10 to about 30 minutes.

The residue is then washed with about 100 to about 500 volumes of acetone per volume of the supernatant liquid of step (b) and dried in vacuum at ambient temperature.

The dried residue is then redissolved in ethanol and filtered on a Sephadex TM column, equilibrated with a sodium phosphate buffer, of 103 cms width and 18–40 cm high.

The Sephadex TM gels, useful in this invention, are known in the art. In the practice of the invention, Sephadex TM gels G-30 and G-100 are preferred.

The sodium phosphate buffer may be used in concentration ranging from about $5 \times 10^{-1}$ to about $5 \times 10^{-6}$ at a PH of about 4 to about 8.

The flux was 10 to 30 drops per minute and the fraction eluting at 5 to 10 mls c/u lyophilized.

On spectrophotometric analysis two protein peaks were observed at 100 to 300 mcg/ml and at 20 to 150 mcg/ml.

The fraction showing the second peak contained the active component whose effect was observed at 10 to 20 days after application to the quinea pig skin.

According to another embodiment of the invention, there is also provided a method of treating human beings afflicted with vitiligo comprising the steps of
  (a) applying an ethanolic solution of the active component obtained according to the invention to the afflicted area;
  (b) followed by exposure of the afflicted area to UV radiation.

According to a preferred mode of the above embodiment, the above ethanolic solution is briskly rubbed onto the afflicted area three times per day until the skin is reddened and the skin is exposed to the UV radiation *one* time per day after one of the applications of the composition of the invention.

Sources of the UV radiation are known in the art and include UV lamps and sunlight.

The following example is illustrative of the invention and is not meant to limit the scope thereof which is solely defined by the claims.

EXAMPLE

The alpha lipoprotein containing extract of human placental cotyledons, prepared according to the invention, was administered, in accordance with the invention, to about 200 persons afflicted with vitiligo, for a period of 4 years and 2 months. Their ages were between 2 and 64 years. They had not undergone any treatment for this affliction prior to administration of the above extract.

The group of subjects was divided as follows:

|  | No. of Cases |
| --- | --- |
| Sex |  |
| Male | 147 |
| Female | 53 |
| Race |  |
| White | 122 |
| Black | 16 |
| Other | 62 |

After treatment, in accordance with the invention, the following results were obtained:

|  | No. of Cases | % of Total Cases |
| --- | --- | --- |
| Patients | 200 |  |
| Repigmented persons | 168 | 84 |
| Entirely repigmented persons | 63 | 31,5 |
| Partially repigmented persons | 105 | 52,5 |
| Persons without repigmentation | 5 | 2,5 |
| Persons who gave up the treatment | 27 | 13,5 |

No local or systemic reactions were observed nor any post-treatment recidivations.

Biopsies of the basal membranes indicated the presence of melanotic pigment, i.e., cure of the illness which is symptomized by the absence of said pigment.

What is claimed is:
1. A method for the treatment of vitiligo comprising:
   (a) isolating protein consisting essentially of alpha-lipoprotein from placental cotyledons, said alpha-lipoprotein having a spectrophotometric protein peak from 20 to 150 mcg./ml.;
   (b) applying the alpha-lipoprotein to the non-pigmented skin areas of a person afflicted with vitiligo; and
   (c) exposing the applied areas to a UV source to effect pigmentation in said areas.
2. The method of claim 1, wherein step (b) further comprises rubbing onto the skin until the skin is reddened.
3. The method of claim 2, wherein the alpha-lipoprotein is an ethanolic solution for step (b).
4. The method of claim 3, wherein the alpha-lipoprotein is present in the solution in an amount of 30% to 50% by weight of the solution.
5. A treatment composition for providing pigmentation to non-pigmented areas of the skin of a person afflicted with vitiligo, said composition consisting essentially of a placental alpha-lipoprotein having a spectrophotometric protein peak of 20 to 150 mcg./ml.
6. The composition of claim 5, wherein the alpha-lipoprotein is present in an amount of about 30% to 50% by weight in the treatment composition.

* * * * *